US008013303B2

United States Patent
Ershov et al.

(10) Patent No.: US 8,013,303 B2
(45) Date of Patent: Sep. 6, 2011

(54) MOBILE REMOTE DETECTION OF FLUIDS BY A LASER

(75) Inventors: Oleg Ershov, Zurich (CH); Alexey Klimov, Kilchberg (CH)

(73) Assignee: Pergam-Suisse AG, Zurich (CH)

( * ) Notice: Subject to any disclaimer, the term of this patent is extended or adjusted under 35 U.S.C. 154(b) by 581 days.

(21) Appl. No.: 12/066,816

(22) PCT Filed: Nov. 28, 2006

(86) PCT No.: PCT/EP2006/011426
§ 371 (c)(1),
(2), (4) Date: May 21, 2008

(87) PCT Pub. No.: WO2007/062810
PCT Pub. Date: Jun. 7, 2007

(65) Prior Publication Data
US 2008/0225273 A1    Sep. 18, 2008

(30) Foreign Application Priority Data
Dec. 1, 2005 (EP) .................................... 05026175

(51) Int. Cl.
*G01J 5/02* (2006.01)
*G01J 3/457* (2006.01)
(52) U.S. Cl. ......... 250/339.07; 250/309.06; 250/339.11; 250/339.13; 356/303; 356/326
(58) Field of Classification Search ........... 250/339.06–339.07, 339.11–339.13; 356/303, 326
See application file for complete search history.

(56) References Cited

U.S. PATENT DOCUMENTS
4,489,239 A    12/1984 Grant et al.
4,853,543 A *  8/1989 Ozdemir ....................... 250/372
(Continued)

FOREIGN PATENT DOCUMENTS
CA    2219335 (A1)    11/1997
(Continued)

OTHER PUBLICATIONS
* Form PCT/IS4/210 (International Search Report) dated Feb. 19, 2007.
(Continued)

*Primary Examiner* — David P Porta
*Assistant Examiner* — Casey Bryant
(74) *Attorney, Agent, or Firm* — Buchanan Ingersoll & Rooney PC

(57) ABSTRACT

Apparatus for remote laser-based detection of a analyte in a remote target region; comprising a reference container for housing a reference substance identical with the analyte; a laser unit which constituted to emit a laser beam of a tuneable wavelength towards the target region to be analysed and along a reference path which passes through the reference container for detecting the reference substance; a laser control means constituted to control wavelength of the laser beam during detection periods such that the laser wavelength is changed to allow detection of an optical absorption profile of the analyte during detection periods; an analytical detection unit which detects light from the target region and generates analytical signals during the detection periods, a reference detection unit which detects laser light passed through the reference container and generates reference signals during the detection periods; and an analysing means constituted to analyse the similarity of the analytical and reference signals or of one or more calculated functions respectively calculated from the analytical and reference signals for determining the concentration of the analyte in the target region.

18 Claims, 12 Drawing Sheets

U.S. PATENT DOCUMENTS

| | | | |
|---|---|---|---|
| 5,015,099 A | 5/1991 | Nagai et al. | |
| 5,157,257 A | 10/1992 | Geiger | |
| 5,200,629 A | 4/1993 | Kaiblinger | |
| 5,250,810 A | 10/1993 | Geiger | |
| 6,509,566 B1 | 1/2003 | Wamsley et al. | |
| 6,518,562 B1* | 2/2003 | Cooper et al. | 250/222.2 |
| 6,664,533 B1 | 12/2003 | van der Laan et al. | |
| 7,355,701 B2* | 4/2008 | Ishibashi | 356/300 |
| 2003/0030001 A1 | 2/2003 | Cooper et al. | |
| 2003/0160173 A1* | 8/2003 | Ershov et al. | 250/338.5 |
| 2003/0218750 A1* | 11/2003 | Friberg et al. | 356/437 |
| 2004/0090628 A1* | 5/2004 | Ershov et al. | 356/438 |
| 2004/0190148 A1 | 9/2004 | Clark et al. | |
| 2005/0162655 A1 | 7/2005 | Nadler | |
| 2006/0244973 A1* | 11/2006 | Yun et al. | 356/511 |

FOREIGN PATENT DOCUMENTS

| | | |
|---|---|---|
| EP | 0 449 573 (A2) | 10/1991 |
| GB | 2 373 096 (A) | 9/2002 |
| JP | 3-277945 (A) | 12/1991 |
| WO | WO 86/02195 (A1) | 2/1986 |
| WO | WO 96/41097 (A1) | 12/1996 |
| WO | WO 97/20167 (A1) | 6/1997 |
| WO | WO 99/54700 (A2) | 10/1999 |
| WO | WO 02/01190 (A2) | 1/2002 |

OTHER PUBLICATIONS

G. Somesfalean et al., "Temporal Correlation Scheme for Spectroscopic Gas Analysis Using Multimode Diode Lasers", Applied Physics Letters, vol. 86, No. 18, Apr. 26, 2005, pp. 184102-1 to 18420-3, XP012065289, American Institute of Physics.

M. Yu Kataev et al., "An Analysis of Methods of Atmospheric Gas Concentration Retrieving From Diode Laser Measurements", 14th Symposium on High-Resolution Molecular Spectroscopy, Proceedings of SPIE, vol. 5311, No. 1, 2003, pp. 280-284, XP-002370999.

A. G. Berezin et al., "Trace Complex-Molecule Detection Using Near-IR Diode Lasers", Applied Physics B—Lasers and Optics, vol. B75, No. 2-3, 2002, pp. 203-214, XP-002371000.

* cited by examiner (a)

(b)

(a)

(b)

MOBILE REMOTE DETECTION OF FLUIDS BY A LASER

The present invention relates to the remote, mobile and optical detection of a fluid in a fluid medium, in particular air. The fluid to be detected may be "gaseous and liquid pollutants" and will be called "analyte" in the following. The analyte may be:
- simple gas molecule, in particular, methane ($NH_3$, CO, $CO_2$, NO, $NO_2$, HF, HCN, etc);
- complex organic molecule, in particular propane, (butane, ethers, spirits, like ethanol, etc);
- aerosol comprising such pollutant as acid, in particular, nitric (chloric, sulphuric) acid.

Measurement method of present invention is based on application of light source, in particular laser. A preferably collimated light beam of applied light source is passed through fluid medium, which may contain analyte under detection and other substances, and hits some target. The target may be:
- topographic object, like grass, trees, bushes, soil, etc.;
- an object, constructed by human, like concrete, brick wall, glass window, house roof, surface of vehicle, etc.;
- dust or aerosol cloud in fluid medium.

Light beam emitted by apparatus is scattered and/or reflected by target. Part of emitted light energy is returned to apparatus and captured by receiving optical system.

Wavelength of light beam coincides with specific feature in absorption spectrum of analyte under detection. The light beam wavelength is preferably changed in vicinity of the absorption specific feature. As a result, parameters of received light are changed after passing through fluid medium containing analyte under detection. Analysis of received light allows to detect analyte and to measure analyte concentration in fluid medium.

The prior art document U.S. Pat. No. 6,644,533 discloses a LIDAR (light detection and ranging). The described apparatus uses a setup, which issues a laser beam at three different wavelengths at the same time, by using a frequency modulation of the laser drive. Absorption of the gas is detected by detecting an unbalance in side bands signals caused by the frequency modulation. The detector result is investigated in the frequency domain.

Further prior art documents are as follows:
U.S. Pat. No. 6,509,566
U.S. Pat. No. 4,853,543
U.S. Pat. No. 6,664,533
U.S. Pat. No. 6,518,562
WO/9720167
U.S. Pat. No. 5,250,810
EP 0 449 573
U.S. Pat. No. 5,157,257
U.S. Pat. No. 4,489,239
WO/9641097
WO/9954700
U.S. Pat. No. 5,015,099
CA 2,219,335
GB 2373096

SOMESFALEAN G ET AL: "Temporal correlation scheme for spectroscopic gas analysis using multimode diode lasers" APPLIED PHYSICS LETTERS, AIP, AMERICAN INSTITUTE OF PHYSICS, MELVILLE, NY, US, vol. 86, no. 18, 26 April 2005 (2005 Apr. 26), pages 184102-184102, XP012065289, ISSN: 0003-6951 discloses the following: The reliability of diode lasers used in spectroscopic applications is limited by their intrinsic multimode and mode-jump behavior when wavelength-tuned by current or temperature. It is reported on a scheme for gas analysis based on temporal correlation between absorption signals from an unknown external and a known reference gas concentration, simultaneously recorded when the diode laser wavelength is temperature-tuned across absorption feature of the gas of interest. This procedure, which does not require any knowledge of the exact spectrum, also eliminates light intensity fluctuations due to the mode competition. The method is illustrated for atmospheric oxygen absorption applied to diffusion measurements.

US 2003/030001 A1 discloses the following: This specification discloses a method and apparatus for the mobile and remote detection of a gas, such as methane, in the atmosphere. The apparatus includes a TDL based Light Detection and Ranging (LIDAR) driven at carrier frequency lying within the absorption line of the gas. The apparatus also drives the TDL with a modulation frequency to generate upper and lower sidebands in the output of the TDL and with a low ramp frequency to sweep the output of the TDL across twice the width of the pressure-broadened absorption line of the gas, preferably the first overtone absorption line in the case of methane detection. The remote detection apparatus includes reference and calibration cells or chambers, and includes a light collector and detectors to detect the quantity and modulation of the light that passes the reference or calibration cells and that is received by the apparatus after reflection back toward the apparatus from an uncooperative target.

KATAEV M YU ET AL: "An analysis of method of atmospheric gas concentration retrieving from diode laser measurements" PROCEEDINGS OF THE SPIE—THE INTERNATIONAL SOCIETY FOR OPTICAL ENGINEERING SPIE-INT. SOC. OPT. ENG USA, vol. 5311, no. 1, 2003, pages 280-284, XP002370999 ISSN: 0277-786X discloses the following: Atmospheric gas tunable diode laser (TDL) monitoring scheme is sensitive, local, real-time and portable. The traditional spectrophotometric methods have more performances for gas analyzing, but are slow in response in high spectral resolution scheme and depend on influences by different gas species. Local measurements of small atmospheric gas components concentration ($CH_4$, CO, etc.) with diode-laser spectrometers are widely used in various of science and technical applications. An inverse task is usually solved by the correlation method (using all the measurement wavelengths) or other methods (for example, the method of fitting of the recorded spectrum under modeling). Each of these approaches has restrictions on retrieving connected with the features of measurement methods used in practice.

The detection of an analyte in fluid medium may be performed by using a mobile vehicle, in particular airplane, helicopter or car, which passes in a distance from the analyte to be detected. Of course, the present invention may also be used on a stationary detecting apparatus. The object of the present invention is to provide a high sensitive apparatus and method for real time mobile remote detection of an analyte, and insensitive to other substances in a fluid medium in order to allow the detection of the analyte in polluted environment, like air around some chemical plants.

The aforementioned object is solved by the subject-matter of the independent claims. The dependent claims are directed to embodiments of advantage.

The detection of an analyte in fluid medium may be performed by using a mobile vehicle, in particular airplane, helicopter or car, which passes in a distance from the analyte to be detected. Of course, the present invention may also be used on a stationary detecting apparatus. The object of the present invention is to provide a high sensitive apparatus and method for real time mobile remote detection of an analyte, and insensitive to other substances in a fluid medium in order to allow the detection of the analyte in polluted environment, like air around some chemical plants.

The aforementioned object is solved by the subject-matter of the independent claims. The dependent claims are directed to embodiments of advantage.

Preferably, the apparatus of the present invention comprises a reference substance. The reference substance is a substance which is identical with the analyte, i.e. has the same spectral optical properties, i.e. the same dependence of absorption and/or transmission and/or reflection properties on wavelength as the analyte. In particular the reference substance is chemically and physically identical (e.g. both are methane). In case the analyte is a fluid, the reference substance is also a fluid (the identical fluid) which is preferably housed in a reference container. The detection of spectral properties includes in particular the detection of an absorption profile but may also (alternatively or additionally) include the detection of a reflection profile. Preferably, spectral optical properties of both the analyte and the reference substance are detected, in particular they are based on the same molecular or atomic transitions. The reference container includes the reference substance to be detected as a reference. The reference container preferably has at least partly transparent wall in order to allow the light beam to pass through the fluid.

Applied light beam unit may be implemented by a broad band light source and for instance a prism. A laser unit having a laser of tunable wavelength is preferred as light beam unit. The laser is preferably a semiconductor laser like a diode laser. Preferably, the laser emits only one laser beam with scanning of radiation wavelength in some range in order to keep the setup simple. However, a laser unit which uses a laser beam, which comprises more than one wavelength sections, may also be used. The optical setup is preferably such that the laser beam is splitted into an optical path, which passes through the reference container (it is reference channel), and another optical path, which is directed to the remote target region (it is analytical channel). The reference container is preferably filled by a gas mixture consisting of the reference substance and some neutral fluid, in particular, nitrogen. Concentration of the reference substance in the reference container is preferably known. In particular, the physical parameters of the gas mixture in container like temperature and pressure are preferably known. Preferably, the concentration and pressure of the reference substance in reference container are set so to achieve a best possible similarity between the absorption spectral properties of the analyte in the analytical channel and the absorption spectral properties of the reference substance in the reference channel. The absorption properties are in particular represented by characteristics of peculiarities of the absorption profile, like shape and/or intensity and wavelength range of detected molecular bands or wavelength and intensity of absorption lines. These features or peculiarities are in particular unique to the analyte and allow preferably to distinguish the analyte from other fluids at the target area. An absorption feature profile (also called "profile of absorption feature") includes in particular a portion of the absorption profile which comprises features which allow for measurement and identification of the analyte. The term absorption features is meant to cover an spectral absorption property which is particular for the analyte. An example for an absorption feature is an absorption line, a group of absorption lines, or an absorption band.

The term "remote" means in particular outside of the apparatus according to the invention. While the reference substance is preferably inside the apparatus (e.g. inside an apparatus body), the analyte is outside thereof. The distance from the apparatus to the analyte may be more than 1 m or 10 m and is typically more than 50 m or 100 m.

Preferably, the laser is a InGaAs laser having for instance a power between 10 mW and 100 mW, preferably below 20 mW in order to avoid any health problems (laser safety class No. 1).

Preferably, the opening angle of the laser beam is less than 0.1° which results in a spot size of about 10 cm in a distance of 100 m.

Preferably, only one spectroscopic mode of the laser is activated, that is realized without any problems for preferably used DFB (Distributed Feed-Back) diode laser.

Preferably, a laser control means is provided. The laser control means comprises preferably hardware, like a laser drive unit and a DAC and software, which controls the laser beam, the drive current, the wavelength and the timing. Preferably, a predetermined control scheme is repeated for every detection period. During this periods, the wavelength of laser beam changes in dependence on the time according to a predetermined function. Preferably, the laser wavelength is changed to cover the full absorption feature profile of the analyte to be detected and additionally a wavelength region outside the absorption feature profile, preferably close to the absorption feature profile. A sweeping of a laser wavelength across the absorption profile is preferably done within the detection period. The detection period is preferably in the range of 1 ms in order to achieve a good spatial resolution during mobile measurements.

Preferably, the laser does not emit a beam during the full detection period. For a subinterval of the detection periods, the laser beam is preferably prevented from issuing the radiation. Thus, preferably, the laser control means works in a pulse mode, which results in a repetitive emission with the laser beam. Preferably, the laser drive current between two adjacent pulses is not zero but above zero and below a threshold value above which the laser starts with emanation. Preferably, the laser drive current is between 50% and 100% of this threshold value. In this way, the temperature of the laser is not destabilized dramatically during laser switching on/off.

The laser wavelength may be changed by changing the laser drive current. Preferably, the wavelength is changed continuously but also a stepwise change of the laser wavelength is possible. Preferably, during a detection period, the laser wavelength is changed within a wavelength range which covers at least partially and preferably fully the profile of absorption feature of the analyte to be detected.

Preferably, an analytical detection unit and a reference detection unit is provided. The analytical detection unit detects light reflected or scattered from the remote target region, for instance a section of a gas pipeline is to be analyzed. The laser beam passes through the analyte before and/or after hitting the target. The laser light (a portion of it) may also be scattered and/or reflected by the analyte, in particular aerosol particles or the target may represent the analyte. A small portion of the light emitted from the target region is captured by the detection unit which may, for instance, include a parabolic mirror or a condensing lens in order to collect the light from the target region and to direct (and focus) the light on the photodetector. The photodetector then generates signals (called analytical signals) due to the detection of the light. Preferably, the timing of the signal generation is divided in detection periods. These detection periods are preferably synchronized with the control of the laser by the laser control means. Preferably, the laser control means covers or scans at least part of the analyte absorption feature profile (and preferably the full absorption profile) during each detection period. Thus, the control of the laser beam and, in particular, the change of wavelength is preferably synchronized with the sampling of signals by the detection unit. The same situation applies preferably for the reference detection unit, which detects light from the reference substance. Preferably, the reference path is set up such that a part of the laser beam passes through the reference unit and in particular the reference substance to the reference detection unit. The reference detection unit detects the absorption profile of the reference substance, which is identical to the analyte. For instance, methane is included in the reference unit in an at least partially transparent container. This allows the detection of methane as an analyte in a remote region.

Preferably, an analyzing means is provided. This analyzing means analyses the similarity of the analytical and reference signals. The laser control means follows preferably for each detection period the same control scheme of timing and wavelength change. Thus, the analytical signals of several detection periods may be averaged in order to increase the signal to noise ratio. The same may be done for the reference signals. However, averaging reduces the local resolution of the analyte distribution and the target region. Next steps of signal processing are normalization and a removal of an offset due to the background light. The analytical and reference signals change in dependence on the time of the detection of the signals and thus represent functions in the time domain. Received analytical and reference functions depends on light source characteristics, i.e. normalized time dependence of radiation power that is named "base-line", and on light absorption by analyte in both channels. Calculation of "base-line" is fulfilled over function parts lying outside analyte absorption feature. Subtraction of calculated "base-line" results in final analytical and reference function depending only on analyte absorption. Preferably, the similarity of the time dependence of final analytical and reference functions is analyzed. This analysis may be done by applying of cross-correlation and auto-correlation as described below in more details with respect to the disclosed detailed embodiments. The result cross-correlation function is proportional to product of analyte concentration in analytical channel and concentration of the reference substance in reference channel, which is preferably known. The linear fit of the cross-correlation function over auto-correlation function calculated for reference function results in calculation of the analyte concentration in analytical channel, i.e. in the target region. The calculated concentration, in particular, represents or is proportional to the number of detected atoms or molecules along optical path length from apparatus to target. If the distance between apparatus and target is known, the analyte concentration per unit volume may be calculated. If there is no similarity between the final analytical and reference functions, i.e. correlation factor equals to zero, then no analyte is detected in the target region. Possible light absorption by other substances leads to another shape of final analytical function, which is usually not correlated with final reference function. Therefore, method applied in present invention allows detection analyte with high selectivity. The use of cross-correlation and auto-correlation functions for determining the similarity between the reference and analytical signals is not obligatory. Other examples are given at the end of the description.

The analytical and reference signals may be in digital or analog form. In particular, the analysis for similarity may be performed by software or analog electronic devices. For instance, the detected analog signals may be converted into digital signal values by means of ADC. The digital values may be arranged, for instance, in arrays. Interpolation may be used between the digital values in order to describe the detected signals in term of functions. Alternatively, a fully analog processing of the detected analog signal in order to analyze the similarity is possible. The terms "functions" and "signals" used herein are meant to cover both alternatives digital and analog representation and processing.

Preferably, the analyzing means is constituted to filter pulses occurring in the analytic signal. Preferably, the analytical means is constituted such that a pulse amplitude value must be arranged between two fixed values. In this way, a suitable filtering may be achieved. Preferably, an analyzing means is constituted such that the pulse slope value has to be in a range between two fixed values. In this way, a suitable filtering can be achieved. Preferably, the analyzing means is constituted such that the signal slope value between two adjacent pulses must not exceed some fixed value. In this way, a suitable filtering may be achieved. Preferably, the analyzing means is constituted such that the standard deviation of signal noise in pulse parts without analyte absorption must not exceed some fixed value. In this way, a suitable filtering may be achieved.

Generally, the application of a pulse filter is preferably. This filter is of advantage for remote mobile measurements of a gas concentration, in particular while the laser beam is reflected by an unknown casual target. Sometimes the reflection factor during such kind of measurement may be changed very fast and the photo detector signal may be distorted dramatically. This may result in a false indication of the gas concentration, e.g. the false detection of a gas leak. Therefore, preferably, the application of a filter, in particular a filter of photo detector pulses, preferably in the analytical channel may be of advantage. In this way, "incorrect" pulses may be excluded from the following data procession. It has been noted that the exclusion of this kind of "incorrect" pulses does not essentially decrease the accuracy of measurement because generally no more than 5% of the detected pulses are distorted. On the other hand, the probability of a false gas leak indication may be diminished.

Preferably, the apparatus comprises a temperature stabilizer for controlling the temperature of the laser, in particular tunable diode laser. It is of advantage to keep the temperature of the laser stable in order to avoid an undesired wavelength shift of the laser beam. Conventionally, this is done by temperature detection and heating and/or cooling of the laser. However, it is preferred to improve further the stabilization. The inventor has found that the temperature stability of the laser may be improved by providing a temperature control based on the detected signals (reference signals or analytical signals). Preferably, the temperature is stabilized based on the reference signals since the analyte absorption feature profile is steadily and easily detectable by the reference detection unit. The temperature control, i.e. heating and/or cooling of the laser is preferably performed such that the absorption profile remains detectable within the detection periods, i.e. the wavelength emitted by the laser during the detection period covers a range which includes the absorption feature. Preferably, the temperature control based on the detection signals (reference signals) is combined with the conventional temperature control which uses a temperature sensor, in particular thermister in order to detect the temperature of the laser. This allows a rough control based on the temperature sensor (in order to set a temperature at the beginning of the detection) and a fine and more sensitive control based on the detection signals (reference signals). The temperature control based on the reference signals allows an improvement of temperature stability of about one order of magnitude as will be discussed in more detail in the detailed description of the embodiments.

Preferably, a particular wavelength control is performed during which the wavelength is not (always) changed smoothly or in (constant) steps during a detection period but there are a plurality of wavelength jumps. This allows measuring a detection signal related to two significantly different wavelengths within a short time scale. In this way, a strong analytical signal fluctuation during mobile measurement due to a fast significant change of reflected light (e.g. due to a change of a target reflectivity) may be eliminated when calculating the concentration of the analyte. The wavelength jumps are preferably performed such that an absorption feature is detected at least twice during a detection period. For this, the laser wavelength jumps between two scanning schemes. In each scanning scheme, the wavelength is controlled to a plurality of wavelength values within a wavelength range. This means for instance that the wavelength smoothly stepwise increases or decreases within the wavelength range for each control scheme. After a predetermined switching time has passed in a first scheme, the control means performs a jump to a second scheme. In the other scheme, the wavelength is again changed smoothly or stepwise for a predetermined switching time. Then the laser control means returns to the first scheme etc. In other words, the laser control means alternates between the first and second schemes. Of course, it is also possible to switch between more than two schemes during a detection period. Preferably, the switching between the schemes is synchronized with the sampling of detection signals so that a number of signals (for instance 1, 2, 3, 4, 5 . . . ) are sampled during each predetermined time.

As mentioned before, the switching between different control schemes allows to detect an absorption effect at the target region at two significantly different wavelengths. This allows eliminating background effects due to a change of reflectivity. For determining the concentration of the analyte, preferably respective functions are determined based on the signals which result from the respective control schemes. These functions are called scheme functions. A further function is preferably calculated based on these scheme functions for instance by calculating a ratio of the scheme functions. The resulting further function is insensitive to changes of a target reflectivity and background light, if they are slower than the predetermined switching time. In case of a speed of detector of 100 km/h, laser beam is displaced over 0.3 mm during switching time of 10 μs between different schemes. It is obvious that change of a target reflection for such displacement of laser beam spot (size is ~10 cm) is negligible for most usual targets. However, the resulting further function depends on difference of the analyte absorption factors between two wavelength ranges of the control schemes. Therefore, this resulting further function can be used for calculation of the analyte absorption in analytical channel, and consequently, for remote determination of the analyte concentration.

Furthermore, a method is provided which performs steps corresponding to the above-mentioned means and units.

In the following detailed description of the present invention further features and advantages of the invention are disclosed.

Figure 9:
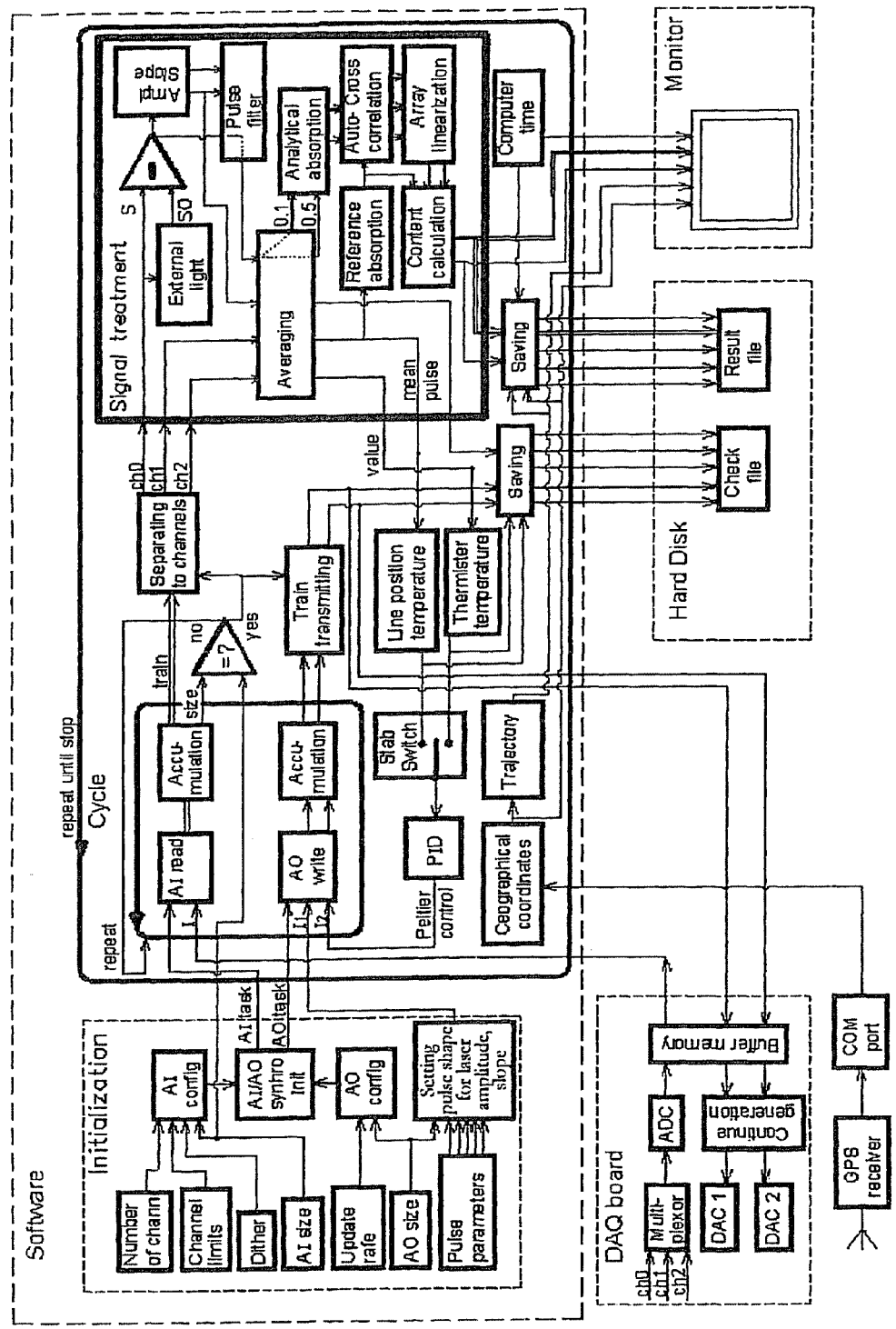

FIG. 8a) shows a laser current supply;
b) shows a resistance-voltage transformer;
c) shows a cooler/heater supply;
d) shows a photodetector signal amplifier;

FIG. 9 is a block scheme of software and hardware and their connection as well as a diagram of data processing;

FIG. 10a) shows a first embodiment of a laser control;
b) shows a second embodiment of laser control;

FIG. 11a) shows a relationship between the detection sample points and the laser wavelength for the first embodiment;

b) shows a relationship between the laser wavelength and detection sample points for the second embodiment;

FIG. 12a) shows detection signal in relationship to the sample points for the first embodiment;

b) shows detection signals in relation to sample points for the second embodiment.

In the following and in the figures, identical reference signs refer to the same means.

Figure 1:
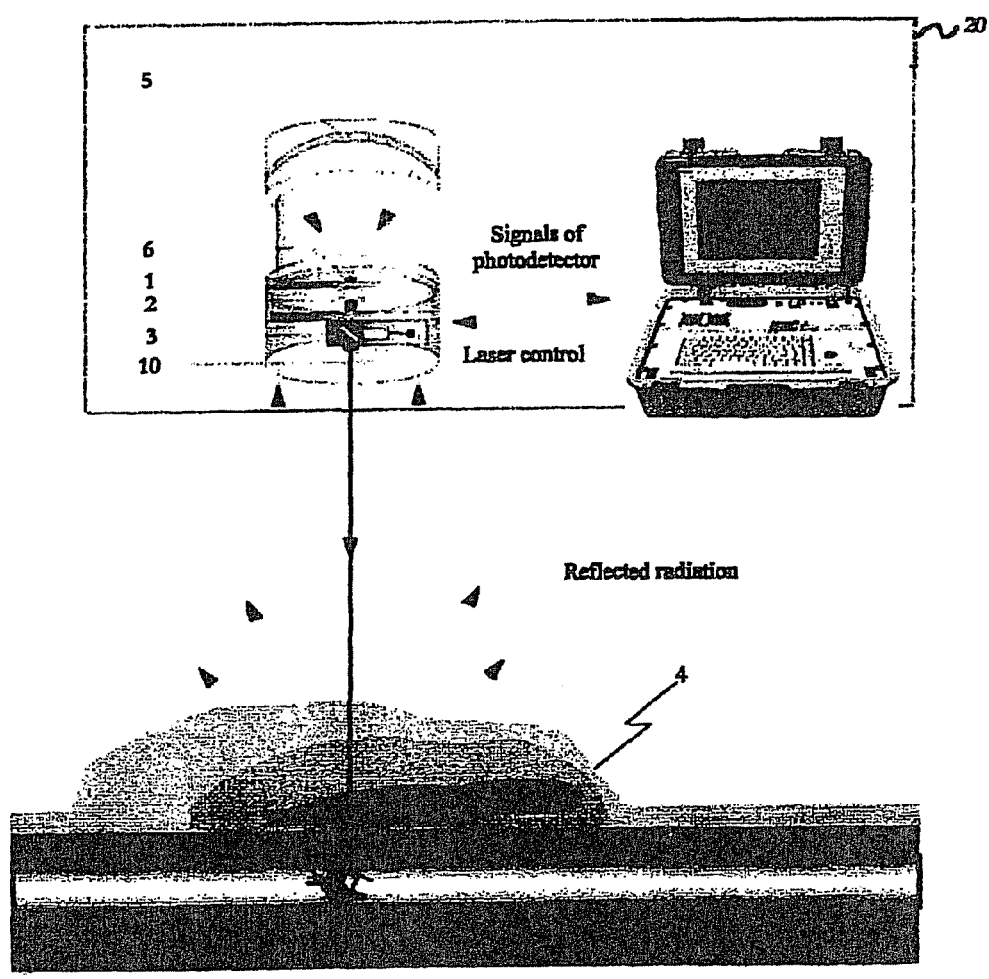
FIG. 1 shows a schematic representation of an embodiment of the present invention and of a target region.
Figure 2:
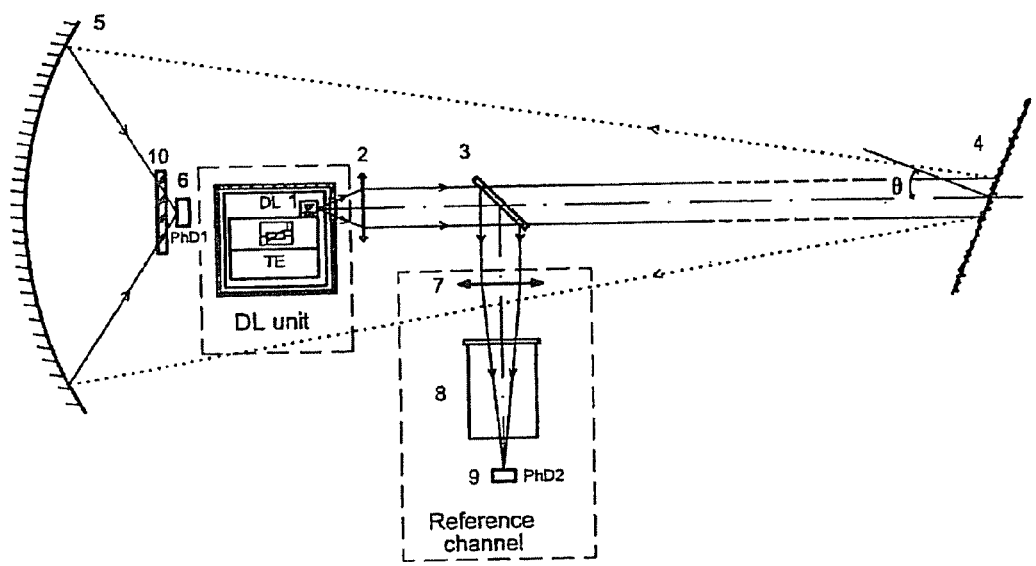
FIG. 2 shows an embodiment of an optical setup used in an embodiment of the present invention.

A schematic representation and a measurement diagram of remote laser methane detector (also called the Detector) are shown in FIG. 1. The optical arrangement of the Detector is shown in FIG. 2. The optical body of the Detector may be installed on a vehicle or helicopter so that the optic axes of the receiving mirror and laser are directed to the target, around which measurements are made. A semiconductor laser, e.g. a tunable Diode Laser (further—DL) emits in pulse mode at 1650 nm, with pulse duration being equal to 1 msec (preferred is a time below 10 ms) and on-off time ratio being 3 (preferred is a on-off ratio between 2 and 10). The radiation of DL 1 is collimated by the objective 2 and directed onto a target object 4 (for instance, soil, grass, trees, concrete, brick wall, aerosol cloud, etc.). Some portion of radiation, scattered by an object, is captured by the receiving parabolic mirror 5, then passed through an optical filter 10 and focused on the photodetector 6 (PD1). The analytical detection unit (also called the analytical optical channel) comprises these components. Some portion of the laser radiation is directed to the reference detection unit (also called the reference optical channel) with the help of beam splitter 3. The reference channel comprises a lens 7, a reference container, e.g. a hermetic cell, filled with methane 8, and the photodetector 9 (PD2). Photodetectors 6 and 9 are assembled together with photocurrent preamplifiers.

Figure 3:
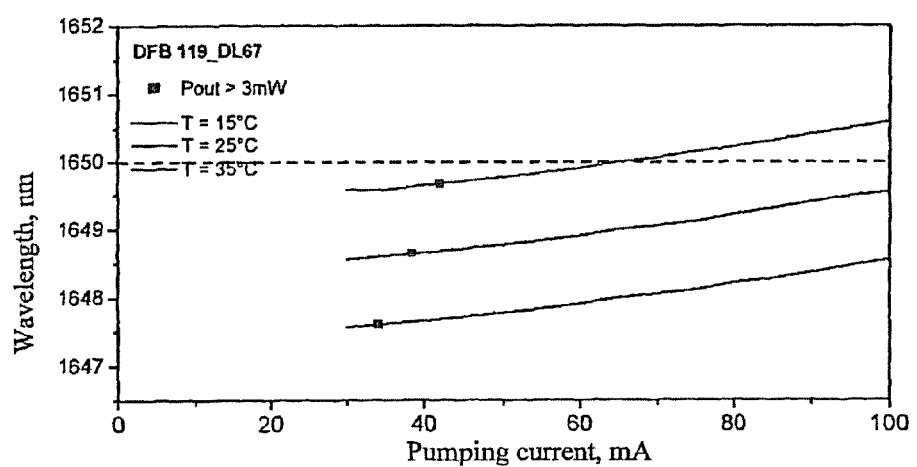
FIG. 3 shows the laser radiation wavelength Vs. pumping current at different laser temperatures.
Figure 4:
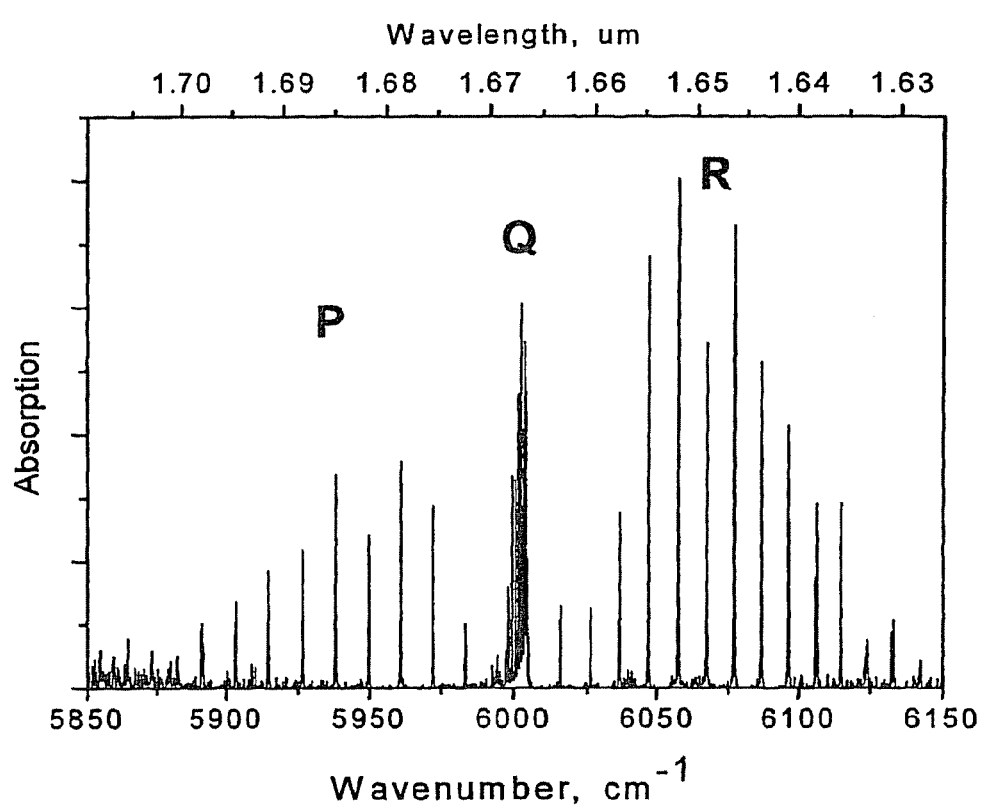
FIG. 4 shows an absorption spectrum of methane in the near influent range and in particular the 1650 nm band.

The DL is an InGaAs/InP type emitting light in the 1650 nm band, which is the first overtone absorption band of methane. The DL is Distributed Feed Back laser mounted on a Thermoelectric Element (further named TE or Cooler/Heater), which allows control and changing of the laser temperature for instance within the range $-10°$ C.$\div +60°$ C. Wavelength and power of the laser radiation may vary depending on laser temperature and drive current. The mean laser radiation power in a chosen mode is near 15 mW. Derivative of radiation wavelength with respect to temperature equals to 0.1 nm/K, with respect to pumping current it equals to 0.01 nm/mA. The laser characteristics of wavelength tuning are shown in FIG. 3. Absorption spectrum of methane in the 1650 nm band is shown in FIG. 4. Three branches of the absorption spectrum are denoted as P, Q, R. One can see that DL radiation wavelength tuning range includes methane absorption lines R5 (1651 nm) and R6 (1648 nm), which may be used as specific absorption features for detection of methane concentration.

Figure 5:
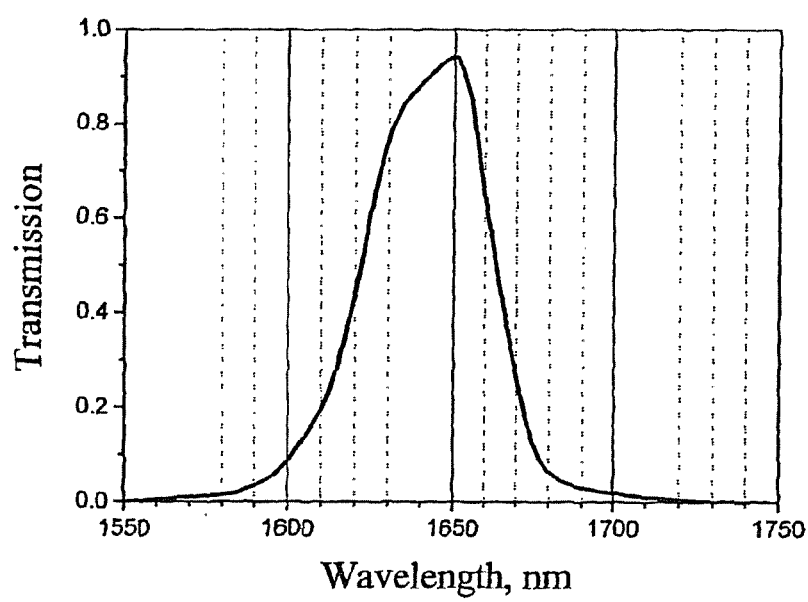
FIG. 5 shows a transmission spectrum of the optical filter used in the detector.

Base parameters of other optical units are following. The receiving parabolic mirror has diameter of 30 cm (preferred is a diameter between 5 cm and 50 cm) and a focal length of 30 cm (preferred is a focal length between 5 cm and 50 cm). Optical aberrations of a parabolic mirror are essentially lower in comparison with a spherical mirror, having the same base parameters. A special optical filter is fixed in front of the photodetector of the analytical optical channel. It is intended for decreasing of preventing background light, for instance, sun illumination. Transmission spectrum of the filter is shown in FIG. 5. The half-width of the filter is preferably greater than the half-width of the methane absorption line profile to be detected. This optical filter allows decreasing sun illumination by 90 times. Transmission of the filter at operation wavelength (1650 nm) is 90%. Laser beam splitter is a glass disk, positioned at an angle of 45° to the laser beam. Sides of the disk are inclined to each other at angle 0.5° for preventing optical interference. Reference channel includes hermetic cell of 70 mm length, filled with the mixture of methane (25%) and nitrogen (75%) at atmospheric pressure. Detection of methane can be realized with the help of R5 methane absorption line, central wavelength of which equals to 1650.9 nm. The absorption factor of reference cell with the gas mixture equals to 0.55 at this wavelength.

Figure 6:
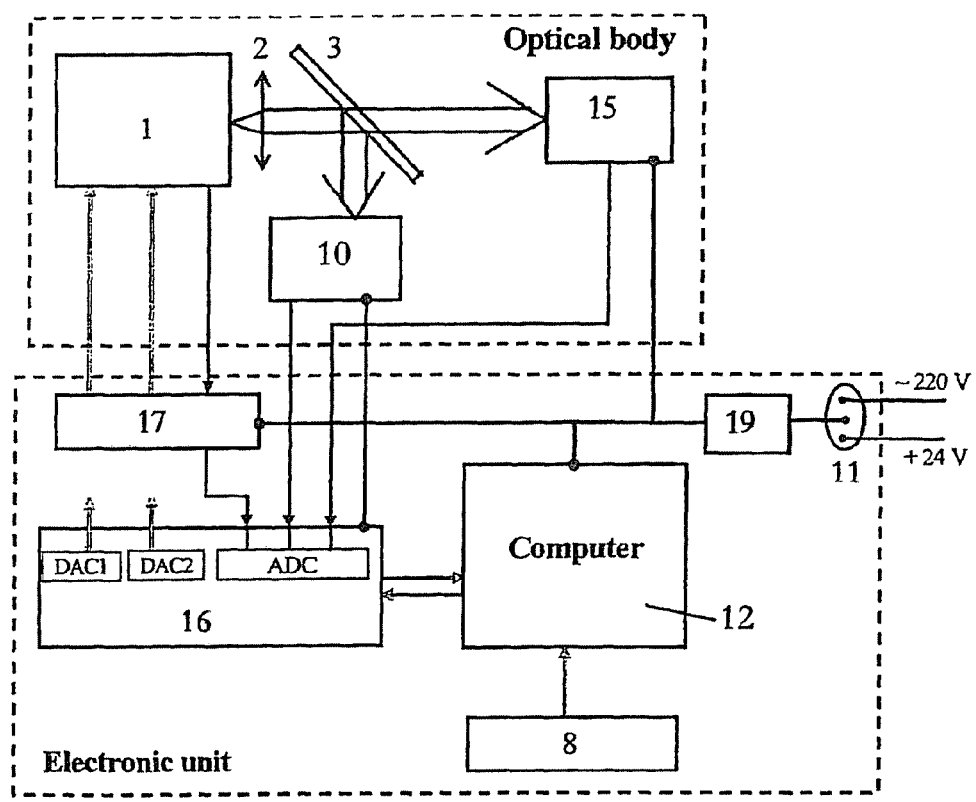
FIG. 6 is a block diagram of an embodiment of the present invention.

The block diagram of the Detector is shown in FIG. 6. Electronic unit of the Detector includes computer 12 (microprocessor module) with multifunction digital board 16 (DAQ board) comprising of several analog-digital and digital-analog converters (DAC1, DAC2, ADC). DL 1 is controlled through analog unit 17. Photodetector signals transformed and amplified by preamplifiers come in ADC of DAQ board directly. Data of GPS receiver 18 come to serial port of computer 12. Power supply of the Detector may be realized from ac voltage 220 V (laboratory variant) or from dc voltage 24 V (field variant) through voltage converter. Laser control and data processing are made using the corresponding software. The signals from the reference detection unit 10 (reference channel) and the analytical detection unit 15 (analytical channel) are converted to digital values by the ADC.

Figure 7:
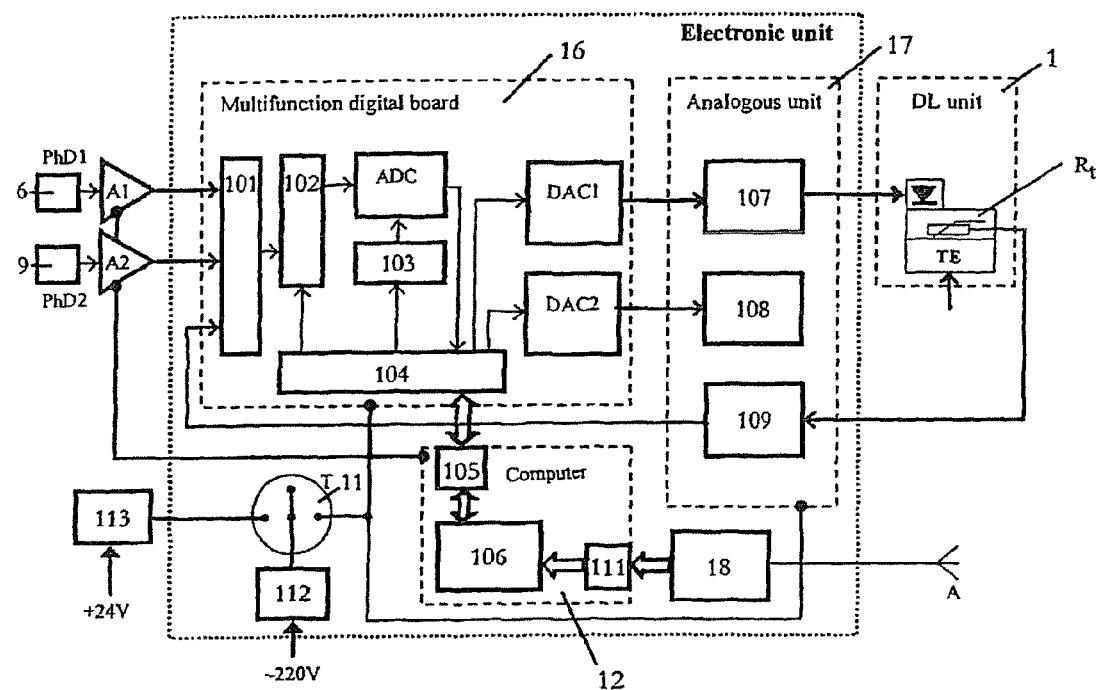
FIG. 7 is a block diagram of the electronic connections and parts used in the embodiment.

Electrical scheme of the Detector is shown at FIG. 7. Detector operation is controlled by the microprocessor unit with built-in industrial computer based on Intel technologies. The components of this computer have increased reliability; hard disk is mounted in shock-isolated module. Industrial color monitor is embedded into the cover of the electronic case.

The device is controlled by multifunctional DAQ board 16. Base parts of the board and specific features of using it are following. The DAQ board involves two output channels (DAC1 and DAC2), input channel (ADC), Multiplexer, Timer, Trigger, Buffer Memory and some other units. DACs and ADC in the DAQ board are of 16-bit resolution, the board digitizing frequency equals to 333 kHz (preferred range is between 100 kHz and 2 MHz). Input voltage range of ADC can be changed with the help of programmable digital amplifier from (−50 mV-+50 mV) to (−10 V-+10 V). The board includes 16 inputs for single ended signals or 8 inputs for differential signals. In the Detector, only three differential inputs are used: Input 1 and Input 2 are amplified signals from photodetectors PD 1 and PD 2 in analytical and reference channels respectively, Input 3 is the signal proportional to resistance of thermister fixed inside DL unit. Multiplexer allows successive connecting of used DAQ board inputs to ADC. The multifunction board 16 also includes Dither 103 that uses for reduction of digital noise in ADC output signals. Two DACs of the board are used for supplying the DL (DAC1) and its Cooler/Heater (DAC2). The DAQ board 16 is installed in the computer PCI bus and connected with Analog unit and photodetector amplifiers A1 and A2 via electric cables. Data exchange between the DAQ board 16 and computer 12 is produced through the board buffer memory 104 and PCI bus. The mode of the Detector controlling and data processing are produced in corresponding software. The sign A designates the antenna for the GPS receiver 18. 105 is the computer PCI bus and 11 is the communication port of the computer 12. The voltage converter 112 converts the voltage from 220V AC to +15V DC and the voltage converter 113 converts +24V DC to +15V DC. T is a toggle switch 11. A1 and A2 are preamplifiers.

Figure 8:
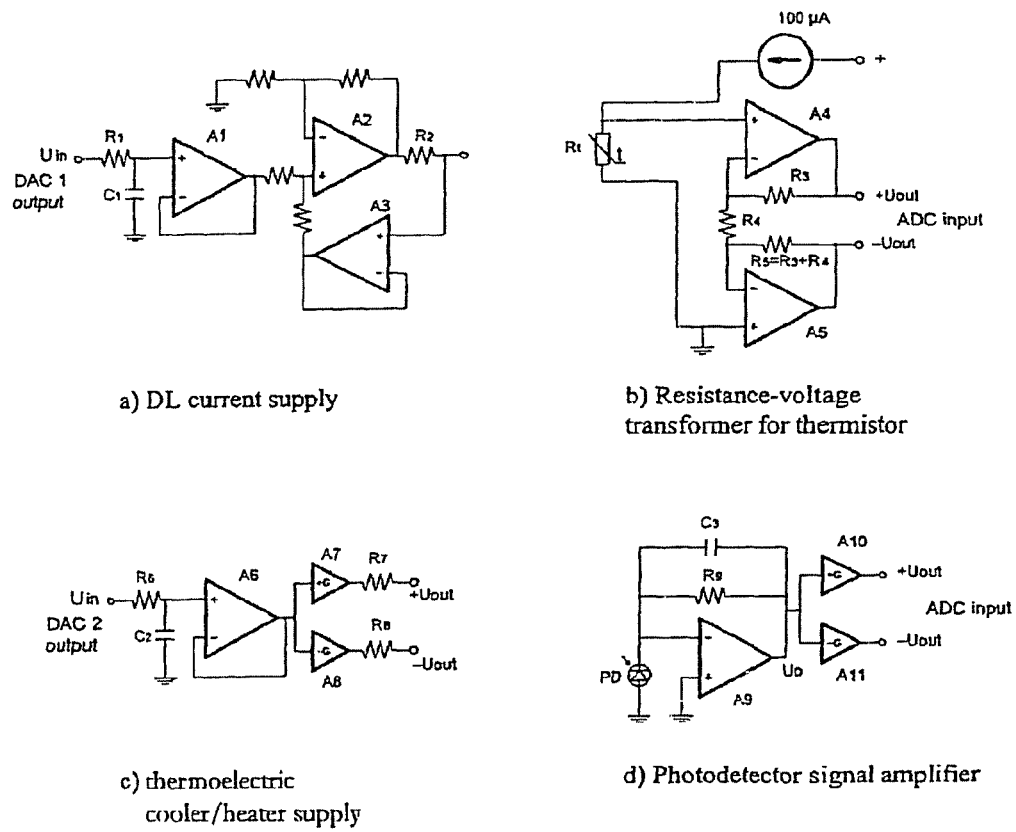

Transformations of output board signals DAC1 and DAC2 and signal for Input 3 are produced in the Analog unit. It involves three analog separate parts: DL Current Supply, Resistance—Voltage Transformer 109 and Cooler/Heater Supply 108. Base electric schemes of these parts are shown at FIG. 8 ($a$, $b$, $c$ accordingly). The DL current supply is performed as follows: signal of a chosen (in the corresponding software) shape is stored in the DAQ board buffer memory 104 and at regular intervals applied to the input of the DAC1. Such a shape may comprise one more control scheme. Output signal of DAC 1 is transmitted to DL Current Supply part 107 of Analog unit 17, amplified and transformed into current pulses feeding the DL. The unit includes three operational amplifiers, product of resistance R1 and capacitance $C_1$ define frequency bandwidth, and resistance $R_2$ defines the current/voltage transformation factor. The output operational amplifier $A_2$ and resistor $R_2$ are chosen thermo stable for preventing drift of output parameters.

Two other parts of the Analog unit (Resistance—Voltage Transformer 109 and Cooler/Heater Supply 108) are intended for stabilization of the DL temperature. The temperature of thermistor having good thermal contact with DL is measured in the Resistance/Voltage Transformer 108 (FIG. 8 ($b$)) including two convenient operational amplifiers and stable current supply, which ensures current of 100 μA supplying the thermister R. The thermister resistance is transformed to voltage in the unit, then transmitted to Input 3 of the DAQ board ADC and transformed to degree value in the instrument software.

Cooler/Heater in the DL unit, designated as TE in FIG. 7, is used for stabilization of the DL temperature by following way. Difference between the current value of the thermister temperature and preset stabilization temperature is transformed in the device program to the DAC2 input value with using of proportional, integrated and differential factors. Then voltage at DAC2 output is transmitted to Cooler/Heater Supply (FIG. 8 ($c$)), which is power amplifier, its output differential voltage supplies the Cooler/Heater resulting in changing DL temperature. The unit includes three convenient operational amplifiers, resistance $R_6$ and capacitance $C_2$ restrict frequency bandwidth, and resistances $R_7$ and $R_8$ restrict maximum output current. Such way of the DL temperature stabilization through software allows realizing also other modes of Cooler/Heater control signal forming (see later).

Base scheme of photodetector transformer-amplifiers A1 and A2 is shown at FIG. 8 ($d$). They transform photo-current signals from photodetectors PD1 and PD2 respectively into differential voltage signals applied to Input 1 and Input 2 of ADC in DAQ board. First stage of the scheme is typical trans-impedance amplifier transforming photocurrent $I_{PD}$ into voltage $V_0$. For ideal scheme does not accounting differential resistance $R_D$ and capacitance $C_D$ of photodiode:

$$V_0 = -I_{PD} * R/(1+j2\pi fRC),$$

where R and C are feedback resistance and capacitance respectively. Amplifier frequency bandwidth is defined by product $R*C$, transfer factor at low frequencies is defined by resistance R. Second stage of the scheme is voltage amplifier. Noise of the scheme depends on $R_D$, $C_D$, R, C and on voltage and current noises of the operational amplifier $A_9$, used in first stage of the scheme. Operational amplifier $A_9$ is AD 829 with voltage noise 1.7 nV/Hz$^{1/2}$ and current noise 1.3 pA/Hz$^{1/2}$. Transfer factor of the scheme is chosen so as its output voltage would be near one of the possible limits of DAQ board ADC amplifier. InGaAs photodiode PD 1 with diameter of sensing area of 2 mm is used in the analytical optical channel of Detector. Noise Equivalent Power (NEP) of this photodetector at operation wavelength equals to $7*10^{-14}$ W/Hz$^{1/2}$. Chosen frequency band of photocurrent amplifier A1 is equal to 10 kHz, so minimum detectable radiation power is equal to 7 pW (standard deviation is accordingly near 2 pW). This value is one of the limiting factors of the measurement sensitivity and dynamic range of presented apparatus. Measurement dynamic range is evaluated by following way. DL radiation power at output of the Detector equals to 10 mW. Reflection factor of some standard topographic targets (such as soil, grass, trees) equals to 0.25-0.35 for chosen operation wavelength range. Calculations and measurements show that laser radiation power on photodetector is approximately equal to 10 nW for standard topographic target remote at distance 50 m, and 2.5 nW for that at distance 100 m. Therefore, the laser radiation can be measured with signal-to-noise ratio:

10 nW/2 pW=5000 for distance 50 m and;

2.5 nW/2 pW=1250 for distance 100 m.

A navigation system receiver, e.g. a GPS (Global Positioning System) receiver or Gallilei receiver is used in the Detector during mobile measurements from helicopter or vehicle to determine the absolute or relative position. This receiver registers current geographical coordinates of the device. GPS receiver may ensure accuracy of relative positioning less then 3 m. External antenna with cable length of 5 m is used for improvement of satellite signal receiving. GPS receiver is connected with communication port of computer for data transmission. Operation of GPS receiver is synchronized with satellite clock and transmits data to computer through 1 sec.

Block-scheme of the Detector software is shown at FIG. 9. The program controls Detector operation and data processing. It is continuously connected with ADC, DAC1 and DAC2 of DAQ board through buffer memory, with communication port of computer for receiving data of GPS receiver, with monitor for displaying results calculated in software, and with Hard disk of computer for writing data files. Initial part of the software includes configuration of ADC, DAC1, and DAC2 with setting of base parameters and its synchronization. Signal processing, DL temperature stabilization, calculation of methane concentration and other operations are produced in base part of the program, which is organized as cycle and finished after pressing the program 'Stop' button. Period of the cycle defines rate of base program operation. It is chosen equal to 0.5 sec for synchronization with GPS receiver operation.

Figure 10:
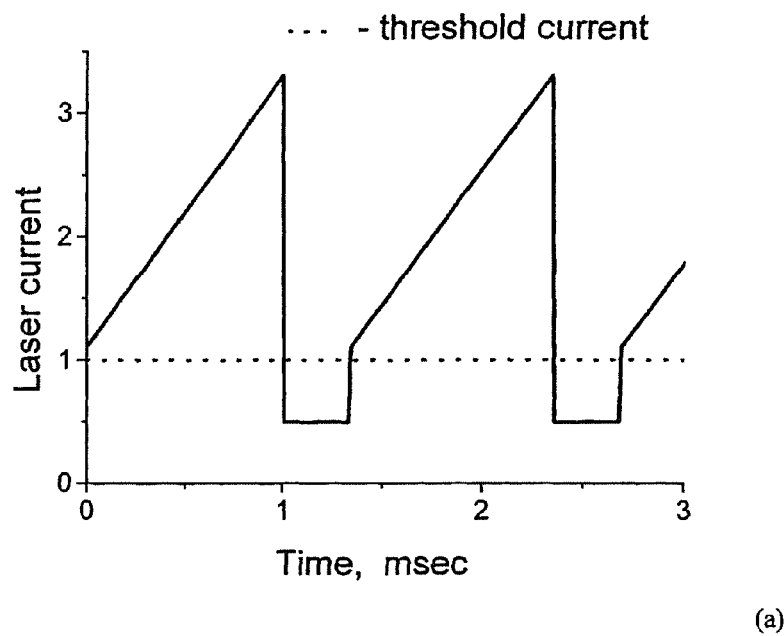
Figure 10:
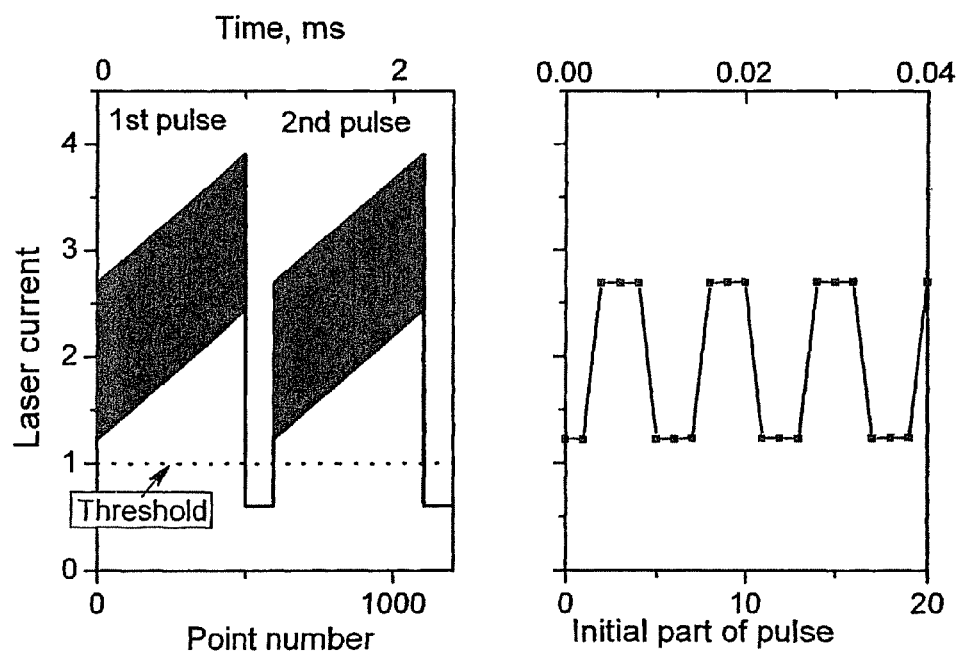

Pattern of current feeding DL is set in initial part of the program ('Setting pulse parameters'), then come to 'AO write' unit in base program cycle, and is consequently applied to the DAC1 of the DAQ board through board buffer memory. As a result, continuous train of current pulses, which shape is shown at FIG. 10, feeds DL. Parameters and specific features of DL current driving are following:

1. Duration of the pulse equals 1 ms, pulse repetition period equals 1.33 ms, so duty factor of pulse train is ~0.75. Since digitizing frequency of used DAQ board equals to 333 kHz, number of points within each pulse is 333, and that between pulses is 111.

2. Two variants of the current pulse shape driven DL are used in the Detector.

2.1. In first variant (see FIG. 10 (*a*)) current pulse is of trapezoid shape, so as DL radiation wavelength is scanned during each pulse, i.e. there is just one control scheme of the laser control means. The scan range of 0.4 nm is chosen in the Detector. This value is approximately three times more than width of a methane absorption line broadened at atmospheric pressure.

2.2. In second variant (see FIG. 10 (*b*)) current driven DL is switched periodically between two ranges, i.e. there is a switching between two control schemes performed by the laser control means. As a result, each pulse is divided in two branches: upper and lower. Each branch in the pulse is of trapezoid form with the same slope. Therefore, DL radiation wavelength is scanned in each branch in different ranges. The time duration between two adjacent switchings equals to 9 μsec (3 points at DAC1 input).

3. DL current between adjacent pulses is not equals to zero; it is a little lower than DL threshold current. It is preferred to diminish logarithm change of DL wavelength at the initial part of pulse due to DL temperature jump, caused by current jump.

Figure 11:
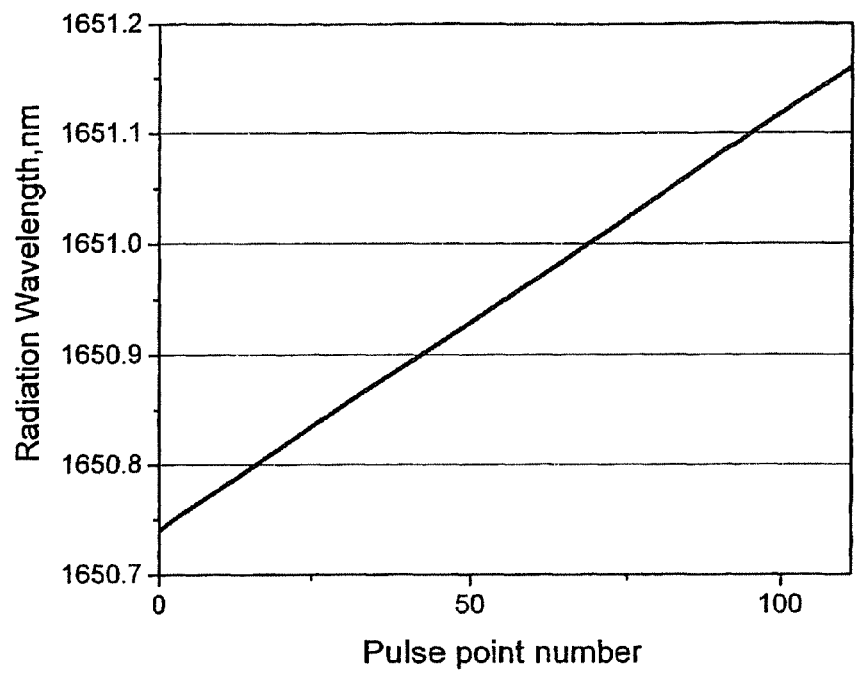
Figure 11:
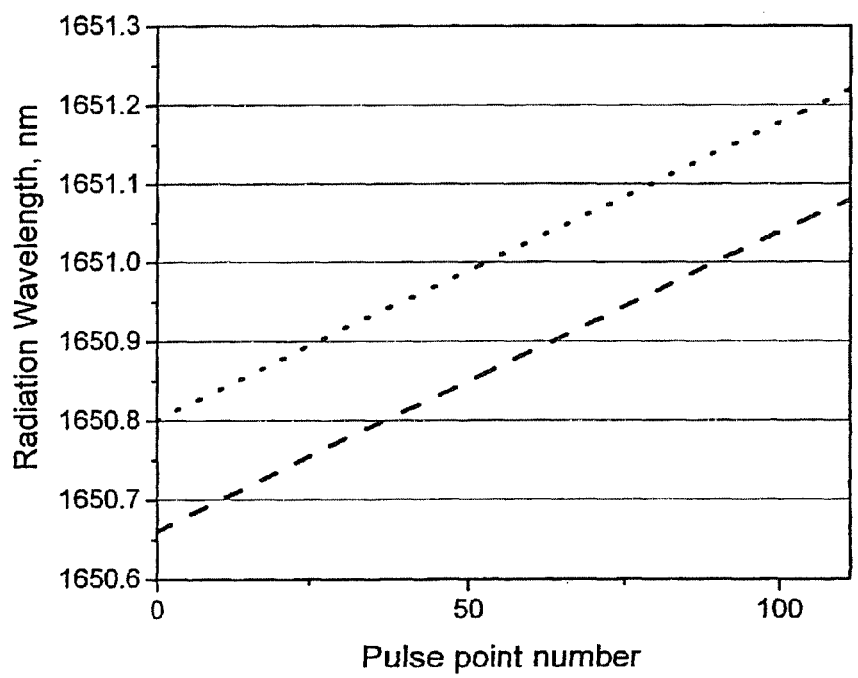

Cooler/Heater of DL allows choosing of DL radiation wavelength scan ranges by changing of DL temperature. DL Cooler/Heater is controlled by DAC2 of DAQ board. Controlling value 'I2' for DAC2 is calculated in the base program cycle, then come to 'AO write' unit, and is consequently applied to the DAC2 of the DAQ board through board buffer memory. For methane detection, DL temperature is chosen so as methane absorption line (such as R5 at 1650.9 nm) is registered near the center of each pulse. Result dependences of DL radiation wavelength from pulse point number for both variants of DL drive are shown at FIG. 11 (*a, b*).

One of noise sources of methane detection is caused by DL radiation wavelength instability due to DL temperature variations. First mode of DL temperature stabilization in the Detector is produced with the help of thermister as described above. This mode ensures stabilization of thermister temperature in laboratory conditions with standard deviation $\sim 2*10^{-3}$ K. This accuracy is restricted by the thermister noise and stability of electric scheme operation. In the field conditions, the results are worse due to wind and variable sunlight, and this temperature stabilization accuracy is not sufficient for field methane detection. The principal disadvantage of DL temperature stabilization with the help of thermister is that the temperature of thermister rather than that of DL is stabilized in this way.

Another mode of DL temperature stabilization is developed in the Detector, in which the control value 'I2' for board DAC2 depends on position of methane absorption line within photodetector signal pulse in reference channel. (The line position is an unbiased criterion of true temperature of DL.) A special calculation procedure of the line position determination is used in the Detector software (see FIG. 9) after processing of photodetector signal in reference channel that come to ADC input. In real measurements with the Detector, DL temperature stabilization is produced by two stages. At first, DL temperature is set roughly with the help of thermister, and then the program is switched automatically to line position stabilization mode for fine stabilization. The signal controlling Cooler/Heater current is formed in the program unit denoted at FIG. 9 as PID, accounting proportional, integrated and differential factors. DL temperature stabilization by means of stabilization of the absorption line position results in the standard deviation ~$2*10^{-4}$ K, that makes negligible the methane detection noise caused by DL radiation wavelength instability.

Transformed signals of photodetectors ('ch0' and 'ch1') and thermister ('ch2') are successively applied to the ADC of DAQ board as described above. Therefore, sampling frequency of each channel is three times lower than the board digitizing frequency and equals to 111 kHz, and duration between two adjacent points at ADC output of each channel is three times higher than that at DACs input and equals to 9 μsec. ADC output signal is transmitted through board buffer memory and come to input of 'AI read' program unit. Output of the program unit is two-dimensional array composed of three columns. These columns are signal values of three DAQ board inputs: 'ch0', 'ch1', 'ch2'. Accumulation of the signals over base program cycle results in array size: 0.5 sec×111000 Hz=55500. Three signal arrays are processed in the program independently, and two-dimensional array is separated into three channels in 'Separating to channels' unit. Thermister signal ('ch2') is averaging over cycle period and come to 'Thermister temperature' unit for calculation of its mean temperature, and then is used in first stage of DL temperature stabilization as it is described above.

Photodetector signal arrays ('ch0' and 'ch1') are separated into pulses in 'Signal treatment' program unit. Each array includes 375 pulses (pulse train) with duration size being 111 points and period size being 148 points. Treatment of reference signal array ('ch1') consists in calculation of pulse averaged over program cycle period. Then this averaged reference pulse is used for calculation of methane absorption line position in 'Line position temperature' program unit. Result value is used in second stage of DL temperature stabilization (see above). Besides, averaged reference pulse is used for calculation of methane concentration in the Detector analytical channel (see below).

Figure 12:
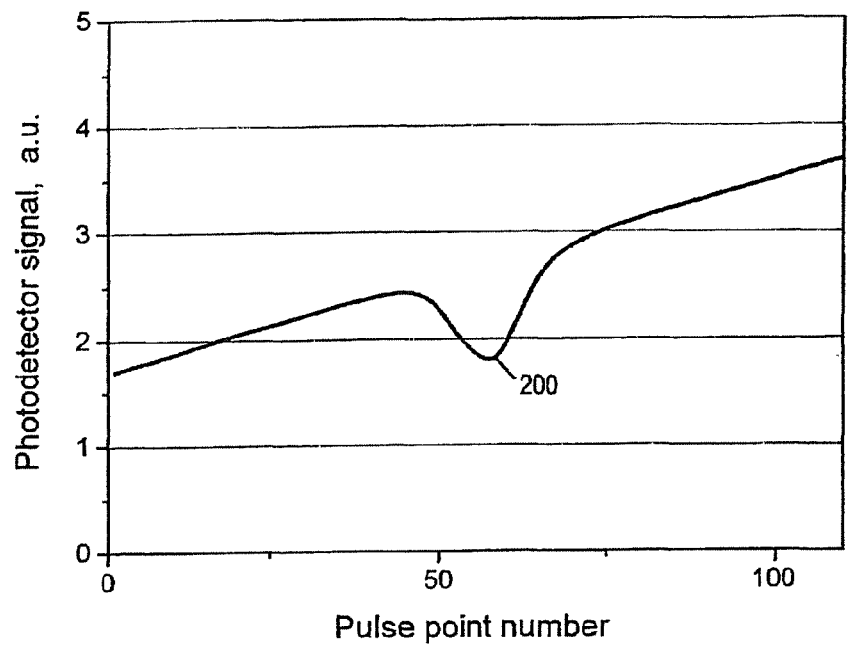
Figure 12:
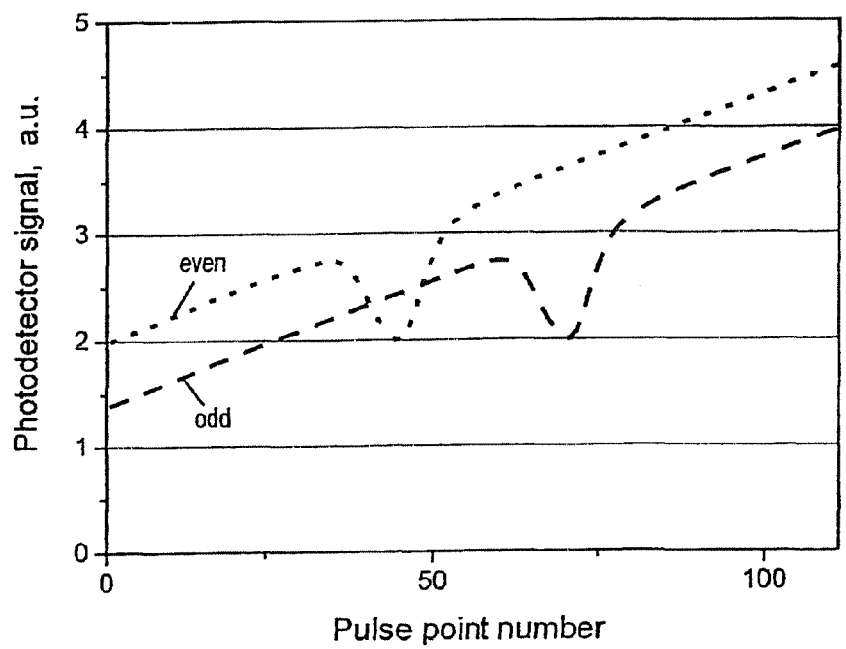

Analytical signal array (S='ch0' values) is processed by one of two ways depending on mode of DL control. If the laser is controlled by current pulses of simple trapezoid shape, photodetector signal of a single pulse for rather high methane absorption is shown in FIG. 12 (a). Signal treatment procedure for this operating mode includes the following steps:

1. Signal values between two each adjacent pulses (received in laser-off state) are interpolated over pulse duration. As a result, auxiliary digital array $S_0$ of full size (55500) is calculated. This array value is proportional to illumination of photodetector by other light sources (such as sun) except laser during program cycle duration (0.5 sec), i.e. represents the background light.

2. Calculation of $S-S_0$ array. This procedure allows excluding of "external illumination" or background light from the signal array.

3. Amplitude and slope of each pulse in pulse train are calculated over initial and final parts of a pulse (see, for instance, FIG. 12a), where methane absorption is absent. The calculated values are needed for the next step 4.

4. Filter of pulses. Some pulses in pulse train may be excluded from following treatment if they are distorted by abnormal conditions of laser radiation reflection. The signal pulses are filtered by the following features:

4.1. Pulse amplitude value must be in range between two fixed values.

4.2. Pulse slope value must be in range between two fixed values.

4.3. Signal slope value between two adjacent pulses must not exceed some fixed value.

4.4. Standard deviation of signal noise in pulse parts without methane absorption must not exceed some fixed value.

5. Averaging of pulses passing through the filter ($<S-S_0>$). This averaging may be produced simultaneously in two modes. First mode is averaging during program cycle duration that is used for calculation of mean methane concentration over 0.5 sec. Second mode is averaging over each 0.1 sec (maximum 75 pulses). In this mode, each pulse train results in 5 averaged pulses that are used for calculation of mean methane concentration over 0.1 sec.

6. Calculation of "Base line" for averaged pulse. The pulse signal values in parts without methane absorption are interpolated over averaged pulse duration resulting in "Base line"—(B).

7. Calculation of logarithm of ratio $<S-S_0>/B$. This normalized value is proportional to methane absorption within wavelength scan $-\psi_1(i)$.

8. Calculation of $\psi_0(i)$ for averaged reference pulse in accordance with procedures of 6, 7 steps.

9. Calculation of cross-correlation function K(i) between functions $\psi_1(i)$ and $\psi_0(i)$ and autocorrelation function A(i) of $\psi_0(i)$.

10. Linearization of calculated function K(i) by function A(i): $K(i)=\sigma*A(i)$. The linearization factor σ is proportional to methane absorption in the Detector analytical channel.

11. The methane concentration $C_a$ in analytical channel is calculated according to the formula:

$$C_a=\sigma*C_r*L_r/L_a,$$

where $C_r$ is methane concentration in the reference cell, $L_r$ is length of the reference cell, $L_a$ is optical pass length in the analytical channel ($L_a=2*L$, where L is the distance from the Detector to target scattered laser radiation).

If the DL is driven accordingly to second variant (switching mode), the time duration between switchings coincides with duration between two adjacent points (9 μsec), so even points form one branch (low), odd points form another branch (high). Photodetector signal of a single pulse for rather high methane absorption is shown in FIG. 12 (b). In this variant of laser control, the treatment procedure includes the following steps (some of the steps are analogous to that in signal treatment of first variant of laser control):

1. Signal values between two each adjacent pulses (received in laser-off state) are interpolated over pulse duration. As a result, auxiliary digital array $S_0$ of full size (55500) is calculated. This array value is proportional to illumination of photodetector by other light sources (such as sun) except laser during program cycle duration (0.5 sec), i.e represents the background light.

2. Separation of odd and even points in the pulse resulting in two numerical arrays O and E. These arrays refer to different frequency ranges of DL radiation.

3. Calculation of $O-S_0$ and $E-S_0$ arrays. This procedure allows excluding of "external illumination" or background light from the signal arrays.

4. Calculation of amplitude and slope of each pulse in pulse train. Amplitude and slope of a pulse are calculated over initial and final pulse parts without methane absorption, it is the mean value between two pulse signal branches.

5. Filter of pulses. Some pulses in pulse train may be excluded from following treatment if they are distorted by abnormal conditions of laser radiation reflection. The signal pulses are filtered by the following features:

5.1. Pulse amplitude value must be in range between two fixed values.

5.2. Pulse slope value must be in range between two fixed values.

5.3. Signal slope value between two adjacent pulses must not exceed some fixed value.

5.4. Standard deviation of signal noise in pulse parts without methane absorption must not exceed some fixed value.

6. Calculation of logarithm of ratio of arrays $E-S_0$ and $O-S_0$: $\chi_1(i)=Ln((E-S_0)/(O-S_0))$. This value is normalized and proportional to difference of absorptions at the branches wavelength ranges. $\chi_1(i)$ is insensitive to any low-frequency signal changes, if characteristic time of the signal changes is essentially more than switching period (9 µs).

7. Averaging of $\chi_1(i)$ function. This averaging is produced simultaneously in two modes. First mode is averaging during program cycle duration that is used for calculation of mean methane concentration over 0.5 sec. Second mode is averaging over each 0.1 sec (maximum 75 pulses). In this mode, each pulse train results in 5 functions $\chi_1(i)$ that are used for calculation of mean methane concentration over 0.1 sec.

8. Calculation of $\chi_0(i)$ for averaged reference pulse in accordance with procedures of 2, 6 steps.

9. Calculation of cross-correlation function K(i) between functions $\chi_1(i)$ and $\chi_0(i)$ and autocorrelation function A(i) of $\chi_0(i)$.

10. Linearization of calculated function K(i) by function A(i): $K(i)=\sigma*A(i)$. The linearization factor σ is proportional to methane absorption in the Detector analytical channel.

11. The methane concentration $C_a$ in analytical channel is calculated according to the formula:

$$C_a=\sigma*C_r*L_r/L_a,$$

where $C_r$ is methane concentration in the reference cell, $L_r$ is length of the reference cell, $L_a$ is optical pass length in the analytical channel ($L_a=2*L$, where L is the distance from the Detector to target scattered laser radiation).

The principal advantage of proposed data processing way is that calculation of gas concentration uses profile of a methane absorption line that allows increasing measurement sensitivity by statistical diminishing of noise. In comparison with methods based on measurement of gas absorption at fixed wavelength, the noise is diminished by factor:

$$n = \frac{\sqrt{\sum \chi(i)^2}}{\chi_0},$$

where χ(i)—data array of the absorption line profile (if laser is controlled by first variant), or data array of the differences of gas absorption factors in two wavelength ranges near gas absorption line (if laser is controlled by second variant). $\chi_0$ is the same value at fixed wavelength, such as at maximum of gas absorption line. The value n may be estimated approximately as: $n=\sqrt{N}$, where N—is number of data array points positioned within absorption line profile. N~25 in measurement procedure, used in the Detector, so applied statistical processing allows increasing measurement sensitivity by a factor of 5 in comparison with methods operating at fixed wavelength.

Another principal advantage of proposed data processing way is application of cross-correlation function of preprocessed analytical and reference signals and following linearization of received function over auto-correlation function of reference signal. This procedure allows essential diminishing of noise and signal distortions that not correlate with methane absorption line in reference signal. Except of increasing of measurement sensitivity this procedure ensures high selectivity of the Detector with respect to other gases (such as water), whose absorption lines may be situated within used wavelength range.

During real mobile measurements the L value (and $L_a$ accordingly) is not known. Therefore, the product $C_a*2*L$ is considered to be measured methane concentration, calculated in ppm*m units (1 ppm is one millionth part of a gas volume content in air). The calculated instantaneous methane concentrations are displayed on the computer screen as a real time graph for both measurement times (0.5 sec and 0.1 sec), with simultaneous data recording into computer hard disk and displaying the alarm message (when registered methane concentration exceed some fixed level of leakage). GPS (Global Positioning System) receiver, integrated into the Detector, transmits data to computer through communication port. Received geographical coordinates and some other data (such as velocity, movement direction and height above sea level) are converted in software to units suitable for presentation. Movement trajectory is calculated for mobile measurements and displayed on the computer screen. Places with increased methane concentration are marked on the trajectory by different colors depending on methane concentration value. Thus measured gas concentration binds to registering geographical coordinates.

Detection limit of measurements approximately equals to standard deviation of noise in ppm*m units. This value depends on photodetector pulse amplitude that defined by distance from Detector to target and reflection factor of target (at stable DL power and diameter of receiving mirror). Detection limit of Detector equals 10 ppm*m for distance L=50 m and standard topographic targets (soil, grass, trees, concrete, brick wall) with reflection factor ~0.3. This value is essentially less than trace methane concentration for this distance: 1.7 ppm*2*50 m=170 ppm*m. Interference of water vapor to methane detection is less than $1/10^4$. Other gases do not interfere to measurements. Therefore, Detector allows detecting methane in air with rather high sensitivity, selectivity, and rate.

The invention is in particular directed to the following:

A LIDAR system based on Tunable Diode Laser unit and methods of operating are disclosed. The apparatus is intended for mobile and remote detection of gas, such as methane, in surrounding air. Laser unit, controlled by computer through DAC, operates in pulse mode with scanning of radiation wavelength in vicinity of the gas absorption feature within each pulse. Additional fast switching of radiation wavelength results in dividing of scanning range into two branches. Laser beam, collimated by optical objective, illuminates a target. Part of laser radiation, which is scattered by target, is captured and registered by the apparatus analytical detection unit. Small part of laser beam deflected by beam splitter passes through reference cell and registered in reference detection unit. Both detected signals come in computer through ADC for processing. Special software filter excludes signal pulses from analytical detection unit, which are distorted by abnormal reflection of laser beam. The rest signal pulses are processed in software resulting in analytical function that depends only on spectral absorption of laser beam. The function is compared with analogous reference function by mathematical methods, preferably by cross-correlation method. The result of signal treatment is total concentration of the gas along optical path from apparatus to target. GPS receiver included to the system allows binding of measured gas concentration with geographical coordinates.

In the following mathematical methods allowing determination of similarity of two functions X(t) and Y(t) are explained in order to make clear that the use of autocorrelation and cross-correlation function is one option to determine the similarity but not obligatory. A simple method for determining similarity is Linear Fit procedure. The general form of the linear fit is given by formula: F(t)=m*X(t)+b, where F represents the output function Best Linear Fit, in is the slope, and b is the intercept. The F(t) function is calculated so as mse (mean squared error) between Y(t) and F(t) is minimum, where mse=$(\Sigma(F_i-Y_i)^2)/N$ (N is size of array functions X, Y, and F).

In this procedure, slope factor m is a measure of similarity of functions X and Y.

Method for determining similarity, which applied in present invention, is following. Final analytical function $\psi_1(t)$ and final reference function $\psi_0(t)$ are calculated at step 7 and 8 in above described signal treatment procedure. (Designations $\chi_1$ and $\chi_0$ are accordingly used for these functions in switching operation mode.) Next possible step in signal treatment would be application of Linear Fit procedure to functions $\psi_1(t)$ and $\psi_0(t)$. But in present invention, firstly cross-correlation function K(t) and auto-correlation function A(t) for reference signal are calculated (step 9 in treatment procedure):

$$K(t)=\int\psi_1(\tau)*\psi_0(t+\tau)d\tau; A(t)=\int\psi_0(\tau)*\psi_0(t+\tau)d\tau$$

Cross-correlation function may be explained as filter for $\psi_1(t)$ function, in which $\psi_0(t)$ function is characteristic filter curve.

Next step of above described signal treatment procedure (step 10) is Linear Fit of K(t) over A(t). The result slope factor σ is measure of similarity of $\psi_1(t)$ and $\psi_0(t)$ functions, and it is proportional to gas concentration in analytical channel.

Additional application of cross-correlation function (in comparison with simple Linear Fit variant) allows to increase "signal-to-noise" value due to excluding of noise from $\psi_1(t)$ function, which is not correlated with final reference function $\psi_0(t)$.

There are some other mathematical method of fitting a function Y(t) by another one X(t). But these procedures consider more complex dependence (than simple linear) between two functions. Some examples are following:

General LS Linear Fit, Polynomial Fit, Exponential Fit, Nonlinear Lev-Mar Fit. Another option is to apply principles of pattern recognition in order to determine the similarity. A determination of the similarity in the time domain is not obligatory but may also be, for instance, performed in the frequency domain after applying a Fourier transformation.

The invention claimed is:

1. An apparatus for remote light-based detection of an analyte in a remote target region, comprising:
   a reference substance identical with the analyte;
   a light beam unit that emits a light beam of a tunable wavelength towards the target region to be analysed and towards the reference substance for interacting with the reference substance;
   a light beam control means for controlling wavelength of the light beam during detection periods such that the light beam wavelength is changed to allow detection of optical properties of the analyte during detection periods;
   an analytical detection unit that detects light from the target region and generates analytical signals during the detection periods,
   a reference detection unit that detects light which has interacted with the reference substance and generates reference signals during the detection periods; and
   an analysing means for analysing a similarity between the analytical and reference signals or of one or more calculated functions, respectively calculated from the analytical and reference signals for determining the concentration of the analyte in the target region by calculating a cross-correlation function between a calculated reference function derived from the reference signals and a calculated analytical function derived from the analytical signals, calculating an autocorrelation function based on the calculated reference function, and calculating the concentration of the analyte based on the cross-correlation function and the autocorrelation function.

2. The apparatus of claim 1, wherein the similarity analysis includes analysing a similarity of a shape of the analytical and reference signals or of the one or more calculated functions in the time domain.

3. The apparatus of claim 2,
   wherein the analysing means cross-correlates the analytical and reference signal or the one or more calculated functions.

4. The apparatus of claim 1,
   wherein the analysing means cross-correlates the analytical and reference signal or the one or more calculated functions.

5. The apparatus of claim 1,
   wherein the light beam control means stops issuance of the light beam for a predetermined time during the detection periods and the analytical and reference detection units generate signals representing light beam-off signals during this time and
   wherein the analysing means uses the light beam-off signals to calculate the one or more calculated functions such that the one or more calculated functions are less influenced by background light than the analytical and reference signals.

6. The apparatus of claim 1, wherein
   among the reference and analytical signals, non-absorption signals are identified which are respectively outside of an absorption feature of the analyte,
   reference and analytical base-line functions are calculated based on the corresponding non-absorption signals, and
   the one or more calculated functions are normalized using the base line functions.

7. The apparatus of claim 1, further comprising:
   a temperature stabilizer for controlling the temperature of the light beam unit based on the reference signals such that an absorption feature maintains light detected by the reference detection unit during the detection periods or during one or more predetermined subintervals of the detection time periods.

8. The apparatus of claim 1, wherein the light beam control means causes a plurality of jumps of wavelength during the detection periods such that detection signals representing an analyte absorption feature are measured at least twice during each detection time period.

9. The apparatus of claim 8, wherein the jumps occur within a time which is less than 100 μs, or less than 20 μs and/or the wavelength jump is greater than half-width of the absorption feature profile, or greater than the detectable width of the absorption feature profile.

10. The apparatus of claim 1, wherein the detection periods are shorter than 2 ms and/or a sampling frequency of the analytical detection unit and the reference detection unit is higher than 50 kHz or 300 kHz.

11. The apparatus of claim 1, wherein the light beam unit is a diode laser, the wavelength of which is controlled by the driving current.

12. The apparatus of claim 1, wherein a navigation system for determining the position of the apparatus and/or the target region is included and wherein the position data are assigned to the concentrations determined at the positions.

13. The apparatus of claim 1, wherein the analysing means filters pulses occurring in the analytical signal.

14. The apparatus of claim 13, wherein the analysing means is constituted such that a pulse amplitude value is in a range between two fixed values.

15. The apparatus of claim 13, wherein the analysing means is constituted such that the pulse slope value is in a range between two fixed values.

16. The apparatus of claim 13, wherein the analysing means is constituted such that a signal slope value between two adjacent pulses is less than or equal to some fixed value.

17. The apparatus of claim 1, wherein the analysing means is constituted such that a standard deviation of signal noise in pulse parts without analyte absorption is less than or equal to some fixed value.

18. A method for detecting a analyte in a remote target region by means of a laser, comprising the steps of:
   providing a reference substance identical with the analyte as reference;
   emitting a light beam of a tunable wavelength by means of a light beam unit towards the target region to be analysed and towards the reference substance for interacting with the reference substance;
   controlling a wavelength of the light beam during detection periods such that the light beam wavelength is changed to allow detection of an optical absorption profile of the analyte during detection periods;
   detecting light from the target region and generating analytical signals during the detection periods by means of an analytical detection unit,
   detecting laser light which interacted with the reference substance and generating reference signals during the detection periods by means of a reference detection unit; and
   analysing a similarity between the analytical and reference signals or of one or more calculated functions, respectively calculated from the analytical and reference signals for determining the concentration of the analyte in the target region by calculating a cross-correlation function between a calculated reference function derived from the reference signals and a calculated analytical function derived from the analytical signals, calculating an autocorrelation function based on the calculated reference function, and calculating the concentration of the analyte based on the cross-correlation function and the autocorrelation function.

* * * * *